United States Patent [19]

Chatterton, Jr.

[11] Patent Number: 4,522,831
[45] Date of Patent: Jun. 11, 1985

[54] METHOD OF TOTALLY SUPPRESSING OVARIAN FOLLICULAR DEVELOPMENT

[75] Inventor: Robert T. Chatterton, Jr., River Forest, Ill.

[73] Assignee: Northwestern University, Evanston, Ill.

[21] Appl. No.: 490,797

[22] Filed: May 2, 1983

[51] Int. Cl.³ ............................................. A01N 31/00
[52] U.S. Cl. .................................................... 514/169
[58] Field of Search ................................ 424/243, 343

[56] References Cited

PUBLICATIONS

Hodgen, Fertile Steril. (1982) 38:281–300.
Koering, In Animal Models for Research in Contraception and Fertility (1979) pp. 187–199, Edited by Alexander.
Nilsson et al, Fertile Steril. (1982) 37:30–34.
Ku et al, Scientia Sinica, vol. XVIII, No. 2, 262–270 (1975).
Mehta, et al, Steroids, vol. 38, No. 6, pp. 679–691 at 680 (1981); vol. 40, No. 1, 65–80, (1982).
Hu et al, WHO Symposium on Steroid Contraception and Mechanisms of Endometrial Bleeding, E. Diczfalusy et al (eds) Geneva, Sep. 12–14, 1979, pp. 191–200.
Chinese J. Obset. and Gynecol. 3: 85–88 (1978).

Primary Examiner—Elbert L. Roberts

[57] ABSTRACT

Ovarian follicular development and related hormonal secretions are totally suppressed for periods of several months or longer by a single intramuscular injection of anordrin administered during menstruation given preferably on the first day of menstrual bleeding. The amount of anordrin administered is in the range of 2 to 10 mg per kg of body weight, and is effective to produce the suppression without administration of additional anordrin by any route. Suppression of progesterone and estradiol secretions is of therapeutic value in the treatment of endometrosis, breast cancer, and other conditions aggravated by ovarian hormones.

6 Claims, No Drawings

METHOD OF TOTALLY SUPPRESSING OVARIAN FOLLICULAR DEVELOPMENT

GRANT REFERENCE

The invention was made in part during research under the Program for Applied Research on Fertility Regulation, Northwestern University, project PARFR-309, under a cooperative agreement with the United States Agency for International Development (DPE-0546-A-00-1003-00).

FIELD OF INVENTION, BACKGROUND, AND PRIOR ART

The field of this invention is the regulation of menstrual cycles, including the control of ovulation, contraception, and ovarian hormone production. The most relevant prior art relates to the contraception drug anordrin.

Anordrin is an A-nor steriod developed in China as an oral contraceptive. See, Ku et al, *Scientia Sinica*, Vol. XVIII, No. 2, 262–270 (1975). When anordrin is synthesized, it is obtained in the form of a mixture of two isomers. The α-form isomer is 2α, 17α-diethynyl-A-nor-5α-androstane-2β,17β-diol dipropionate, and the β-form isomer is 2β,17α-diethynyl-A-nor-5α-androstane-2α,17β-diol dipropionate. As indicated by Ku et al, above cited, the 60 , β-isomer mixture has been used in China as an oral contraceptive, and referred to as AF-53, or as Anti-Fertility Tablet No. 53.

The β-isomer has a lower level of activity with respect to ovarian functions than the α-isomer. The α-isomer anordrin can be readily separated from the β-isomer to obtain the α-anordrin as a pure crystalline compound. See, for example, Mehta, et al, *Steroids*, Vol. 38, No. 6, pages 679–691, at 680 (1981).

Researchers in the People's Republic of China have studied the endometrial and hormonal changes induced by α,β-anordrin in women using post-menstrual pre-ovulatory regimens of oral administration with varying dose levels and administration schedules. See Hu et al, *WHO Symposium on Steroid Contraception and Mechanisms of Endometrial Bleeding*, E. Diczfalusy et al (eds) Geneva, 12–14 Sept., 1979, pages 191–200. Hu et al concluded from the data presented that ovulation can be inhibited and/or luteal function depressed when administration of anordrin is started in the period following menstruation but prior to ovulation. It was observed that when anordrin is started up to three days prior to ovulation that ovulation may be inhibited, and that a suppressive effect on the development of Graafian follicles may be observed. Hu et al, above cited, page 198.

Chen, C. H. and Chen, Y. have published a study of urinary pregnanediol measurements following α,β-anordrin administration to women postmenses, using varying dose levels and administration procedures. *Chinese J. Obset. and Gynecol.* 3: 85–88 (1978). The doses of α,β-anordrin varied from 0.5 mg to 4 mg per day, starting from 1 to 6 days after menstruation and continuing for 7 to 9 continuous days. The administration procedures included an intravaginal capsule, a suppository capsule, and an oral capsule. The study confirmed that α,β-anordrin administered during the phase of follicular development could inhibit ovulation. The study also indicated that the time of ovulation could be determined by measurements of urinary pregnanediol. Urine collections were continued following the last dose of the α,β-anordrin until menstruation occurred; a delay in ovulation occurred in only about 10% of women in these studies.

SUMMARY OF INVENTION

This invention is based on the discovery of a new effect from α-anordrin administration: the total suppression of ovarian follicular development and related hormonal secretions. To accomplish this result, the time, dose level, and mode of administration are important parameters.

As far as it is known, no prior studies have been made or published in which anordrin was administered to the female subjects during menstruation. Further, although several modes of anordrin administration in addition to tablets have been tested, the effect of a single intramuscular injection (I.M.) in women or experimental animals has not been reported for any part of the menstrual cycle. Anordrin has been administered in a sesame oil vehicle by subcutaneous injection (S.C.) to laboratory animals. Mehta, et al, *Steroids*, Vol. 38, No. 6, 679–691 (1981); and Mehta, et al, *Steroids*, Vol. 40, No. 1, 65–80 (1982). The published results of these studies, however, do not relate to nor suggest the method of the present invention.

In accordance with the present invention, ovarian follicular development and related hormonal secretions are totally suppressed by administering to a woman during a period of menstruation a first dose of α-anordrin of from 2 to 10 milligrams (mg) per kilogram (kg) of body weight. The administration is by intramuscular injection and is given on the first day of menstrual bleeding, or within two days thereafter providing menstruation is continuing. The thus injected anordrin is effective to produce the total suppression for at least the equivalent of two complete menstrual cycles, that is, 56 days or longer, without administration of additional anordrin by any route.

DETAILED DESCRIPTION

The term "anordrin" as subsequently used herein and in the claims is defined to mean α-anordrin (2α,17α-diethynyl-A-nor-5α-androstane-2β,17β-diol dipropionate). This compound is distinguished from the β-form isomer, 2β,17α-diethynyl-A-nor-5αa-androstane-2α,17β-diol dipropionate. The method of this invention uses α-anordrin in substantially pure crystalline form and, preferably, substantially free of the β-form isomer. All dose levels given herein are therefore with reference to the-α-form (anordrin).

Anordrin, both in pure form and in admixture with the β-isomer is understood to be produced in the People's Republic of China, and is also available in limited supply through the World Health Organization, Geneva, Switzerland. As far as is known, anordrin is not yet commercially available in the United States. However, it can be readily prepared from published procedures. One suitable procedure is that of Crabbe et al, as published in *Steroids* 33, 85 (1979). Mehta, et al, followed the method of Crabbe et al to produce a racemic α,β-isomer mixture from which pure crystalline anordrin was obtained by column chromatography on silica gel using a hexane-acetone solvent system. See *Steroids*, Vol. 38, No. 6, 679, at 680 (1981).

To prepare the anordrin for I.M. injection, it is obtained or prepared, and combined with a suitable carrier. Since anordrin is oil soluble, vegetable oil vehicles, such as sesame oil, can be used. Depot-type highly retardent vehicles are not desirable, since relatively rapid absorption of the administered anordrin is desired. It will be understood, however, that other intramuscular vehicles and carriers can be used besides vegetable oils. In general, preferably the carrier can be an injectable liquid in which the anordrin is soluble and from which it is absorbed by the body.

For the purpose of the present invention the anordrin is administered during menstruation, preferably on the first day of menstrual bleeding, or at least within 2 days thereafter while menstruation is continuing. During this period, as has been discovered in connection with the development of the present invention, the ovarian follicular and hormonal system is exquisitely sensitive to the suppressive effects of anordrin. Thus, a single IM dose can result in total suppression of follicular development and related hormonal activity, such as the secretion of progesterone and estradiol. Further, the suppression can last for the equivalent of several menstrual cycles without administration of additional anordrin.

More specifically, the indicated dose by I.M. injection is within the range from 2 to 10 mg of anordrin per kg of the woman's body weight. Further, based on present information, it appears that the preferred dose level will be from about 4 to 8 mg anordrin per kg of body weight. Using the preferred dose level and administering the injection on the first day of menstruation, follicular recruitment can be avoided, no follicular development will occur, and no concomitant secretions of the ovarian hormones. This suppression, depending on the dose size, can continue for at least the equivalent of two cycles (56 days), or for cycles of three (84 days) or longer term. Resumption of the menstrual cycle as signaled by ovulation is, in effect, postponed by the method of this invention. Such suppressive postponement of ovulation has been obtained in female monkeys as the experimental animal for woman for periods of 4 to 5 months. It is believed that even longer periods of suppression are feasible.

Where the method is being applied as part of a therapy for endometrosis, breast cancer, or other condition aggravated by the production of ovarian hormones, it will usually be desirable to continue the suppression by subsequent intramuscular injection of an anordrin dose corresponding to the initial dose. To maintain and continue the total suppression, the second dose should be administered before the resumption of follicular recruitment. If this is not done and the suppressive effect has diminished so that follicular development occurs, then the cycle will continue for the post-menstruation phases. Ovulation will occur normally and the post-ovulation part of the cycle will be normal. Upon the next menstruation, the method of this invention can be reinstituted using the same procedure. However, an interruption in suppression will allow some progesterone and estradiol to enter the system. However, if as preferred, a second dose is administered at a time several months after the initial dose and while follicular development is still repressed, the suppressing effect can be continued without interruption. For example, where the initial dose provides an effective supresion over substantially longer than 56 days, the second dose can be administered at a predetermined "safe" time, such as on day 56.

Available experimental evidence indicates that discontinuance of the suppression can be done safely. Even after long-term suppression, a return to hormonally normal menstrual cycles can be expected. The suspended cycle will be resumed without menstruation, normal follicular recruitment and development occurring, followed by normal ovulation, and a normal post-ovulation period. If no additional dose of anordrin is administered, menstruation will then occur at the beginning of the next cycle, and subsequent cycles will also be normal. The method of this invention and its experimental basis are illustrated by the following examples.

EXPERIMENTAL EXAMPLES

Anordrin (2α,17α-diethynyl-A-nor-5α-androstane-2β,17β-diol dipropionate) was prepared as follows:

Step 1: 17β-hydroxy-5α-androstan-3-one (1)to 17β-acetoxy-5α-androstan-3-one (2)

Excess acetic anhydride is added to a solution of 17β-hydroxy-5α-androstan-3-one (Aldrich, Milwaukee, Wis.) in dry pyridine. The reaction mixture is allowed to stir overnight at room temperature. Following neutralization with ice-cold 10% HCl, the mixture is extracted with $CHCl_3$. The organic layer is washed with 10% HCl, 5% $NaHCO_3$, saturated NaCl and dried over anhydrous $MgSO_4$. Evaporation of the solvent yields 2 in greater than 95% yield.

Thin-layer chromatography (TLC) is performed in hexane/acetone (3/1). 2 may be recrystallized from the same solvents. NMR: 4.63 (t, 17 H), 2.03 (s, $COCH_3$), 1.02 and 0.81 (2s, 18 and 19-Me).

Step 2: 2 to 17β-acetoxy-2,3-seco-5α-androstane-2,3-dioic acid (3)

This transformation is carried out according to procedures described by Scribner[1](Ref. 1). 11.12 g 2 are dissolved in 75 ml of acetic acid, 2.5 ml $H_2O$, and 0.75 ml methanol, and heated to 60° C. with stirring. A solution of 13.5 g $CrO_3$ in 30 ml acetic acid and 25 ml $H_2O$ is added slowly so that the temperature remains between 60°–65° C. The reaction mixture is then maintained at this temperature for 2½ hours. 75 ml of $H_2O$, preheated to 60° C., are added and the reaction is allowed to stand at room temperature overnight. Filtration and washing of the filter cake with water gives, after drying, 4.54 g (36%) of white crystalline 3, m.p. 226°–228° C. NMR: 4.63 (t, 17 H), 2.03 (s, $COCH_3$), 0.82 and 0.78 (2s, 18 and 19-Me).

Step 3: 3 to 17β-acetoxy-Anor-5α-androstan-2-one (4)

The A-ring of the steroid is reclosed to a five-membered ring according to Scribner's procedure[1]. A sand-bath and short-path (5 cm) right-angle tube are used instead of a Woods metal bath and Claissen adapter, respectively. 7.28 g 3 are dissolved in 60 ml acetic anhydride and refluxed for 2 hr. The reflux condenser is replaced by a distillation head, and 60 ml of liquid are collected at atmospheric pressure. The distillation head is replaced by the short-path tube and a collecting flask, and the dark green distillation residue is slowly heated to 260° C. with 10–15 mm vacuum applied from the side-arm of the receiving flask. The temperature is maintained between 260°–270° C. for 1½ hr. The vacuum is then increased, and heat is applied to the side-arm to force the distillation into the receiving flask. The crude product, a yellow solid, is dissolved in $CHCl_3$ and washed with 5% $NaHCO_3$ and saturated NaCl. After drying and stripping of the solvent, 4.32 g 4 are obtained (71%). NMR: 4.63 (t, 17 H), 2.01 (s, $COCH_3$), 0.85 and 0.81 (2s, 18 and 19-Me).

Step 4: 4 to 17β-hydroxy-Anor-5α-androstan-2-one (5)

4 is dissolved in 1N NaOH in 80% ethanol and stirred, at room temperature, for two hours or longer.

The reaction mixture is neutralized with ice-cold 1N HCl and extracted with ethyl acetate. Following drying over MgSO$_4$ and stripping of the solvent, 5 is obtained in approximately 95% yield. m.p. 189°–192° C. (lit. m.p. 191°–194° C.[2]). NMR: 0.85 and 0.76 (2s, 18 and 19-Me).

Step 5: 5 to Anor-5α-androstan-2,17-dione (6)

Jones reagent (13.36 g CrO$_3$ in 11.5 ml conc. H$_2$SO$_4$, diluted to 50 ml with H$_2$O) is added dropwise, with stirring, to a solution of 5 in acetone at 0°–5° C. until a reddish color remains. After approximately 30 minutes, isopropanol is added to remove excess Jones reagent. Following addition of cold water, the reaction mixture is extracted with ether. The ethereal layer is washed with 5% NaHCO$_3$, dried over MgSO$_4$, and stripped.

The white solid obtained is recrystallized from ether to give 6. m.p. 170°–171° C. (lit. m.p. 171°–173° C.[2]). NMR: 0.89 (s, overlapping 18 and 19-Me). Step 6: 6 to 2α,17α-diethynyl-Anor-5α-androstan-2β,17β-diol (7)

Ethynylation of 6, carried out according to Crabbe's procedure[3], yields a mixture of epimers at the C-2 position, as shown by NMR. Although repeated recrystallization from CH$_2$Cl$_2$/petroleum ether can result in pure 7, chromatography of the esterified Anor steriods separates the epimers more efficiently. Dry acetylene gas is bubbled through a solution of 9.3 g lithium acetylide-ethylene diamine complex in 16 ml anhydrous DMSO for 20 min. with stirring. The reaction mixture is cooled to 0°–5° C. and 3.26 g 6 in 96 ml anhydrous DMSO is added. After bubbling through acetylene gas for an additional 30 min., the reaction is quenched with 10% aqueous ammonium chloride, filtered, and extracted with dichloromethane. The organic layer is washed with water, treated with decolorizing charcoal, dried, filtered, and stripped to yield 2.54 g (66%) of a pale yellow oil. NMR: 2.56 (with shoulder) and 2.49 (-CCH), 0.93 (with shoulder) and 0.85 (18 and 19-Me). Step 7: 7 to 2α,17α-diethynyl-Anor-5α-androstane-2β,17β-dipropionate (8)

Crabbe's procedure[3] is used to esterify 7. Excess propionic anhydride (15 ml) is added to a solution of 1.6 g 7 in 20 ml dry pyridine. The reaction mixture is refluxed for 15–17 hr at 112°–117° C., yielding a dark brown solution. Methanol is added to the cooled reaction mixture to decompose excess propionic anhydride. After addition of ice water and neutralization with 10% HCl, the solution is extracted with dichloromethane. The organic layer is washed with 10% HCl and water, treated with decolorizing charcoal, dried, filtered, and stripped, yielding 1.46 g of a light brown oil. Recrystallization from methanol at this point to yield pure anordrin has not been successful. However, chromatography over silica gel with hexane/acetone (10/1) as the eluting solvent does separate the C-2 epimers with the 2β-epimer being eluted first. The steroids are identified by chromatographing a small aliquot of each fraction from the column on TLC (hexane-acetone, 3:1) and observing the separated compounds by charing with sulfuric acid.

Fractions containing anordrin are combined, the solvent stripped, and the resulting solid recrystallized from methanol. m.p. 152.0°–152.5° C. (lit. m.p. 152.5°–153° C.[3]) NMR: 2.58 and 2.54 (2s, -CCH), 1.13 (t, 2 -CH$_2$CH$_3$, 8 Hz), 0.86 and 0.84 (2s, 18 and 19-Me). Gas chromatography on an OV-1 liquid phase on Supelcoport (Supelco, Bellefonte, Pa.) at 230° gives retention times for the 2α and 2β epimers of 24 min and 10.5 min, respectively.

Treatment of monkeys.

Cynomolgus monkeys (*macaca fascicularis*) were quarantined for 2 months for observation. Thereafter they were placed in cages with collection trays fitted with a screen to allow collection of urine without contamination by food pellets or feces. Urine was collected daily from the trays containing 100–200 mg of sodium metabisulfite as a preservative. The volume of urine was measured, and aliquots of urine were stored at 4° C. for subsequent radioimmunoassay for pregnanediol glucaronide.[4] In addition, vaginal smears were taken on Monday, Wednesday and Friday each week to check for bleeding. Menstrual bleeding could also be detected by the presence of blood in urine collection trays. Control cycles before treatment in 8 monkeys averaged 31 days. The cynomolgus monkeys in the controlled environment of the animal resource center exhibit regular menstrual cycles throughout the year as reported by others.[5,6]

For injection, anordrin, prepared as described above, was dissolved in sesame oil (Fisher Scientific, Pittsburgh, PA) in a concentration of 25 mg/ml and injected intramuscularly in the gluteus maximus in doses of 4 and 8 mg/kg body weight, respectively, in two monkeys. Other monkeys received 0.5 and 1.0 ml of the sesame oil vehicle only.

Monkeys given the 4 and 8 mg/kg doses of anordrin had no menstrual periods for 119 and 135 days, respectively. On day 18 or 19 of the menstrual cycles of each monkey the ovaries were observed directly by laparotomy; no corpora lutea indicative that ovulation had occurred were present, and visible follicles of a preovulatory size were also undetected. The ovaries appeared inactive, as they would postmenopausally in women. Assay of pregnanediol as a means of detecting the occurrence of ovulation also revealed no hormonal activity associated with ovulation.

Other monkeys in which more than three months of amenorrhea was induced by anordrin treatment were shown by hormonal criteria to have normal ovulatory cycles either following the first or second menstrual period after the period of amenorrhea.

References

1. Scribner, R. N. in *Organic Reactions in Steroid Chemistry*, v. 2, ed J. Fried and J. A. Edwards. New York, Van Nostrand Reinhold, 1972, p. 409.
2. Minson, M. and J. Jacques, Bull Soc Chim Fr, 1965, p. 71.
3. Crabbe, P. et al, Steroids, 33:85, 1979.
4. Chatterton, et al, Fertil Steril, 37:361, 1982.
5. Macdonald, Fertil Steril 22:373, 1971.
6. Goodman, et al, Proc Soc Exp Biol Med 155:479, 1977.

I claim:

1. The method of totally suppressing ovarian follicular development and related hormonal secretions, comprising administering to a woman having menstrual cycles during a period of menstruation a first dose of from 2 to 10 milligrams (mg) per kilogram (kg) of body weight of 2α,17α-diethynyl-A-nor-5α-androstane-2β,17β-diol dipropionate, said administration being by intramuscular injection and being given on the first day of menstrual bleeding or within two days thereafter while menstruation is continuing, the injected amount of anordrin being effective to produce said total suppression for over 56 days without administration of additional anordrin by any route.

2. The method of claim 1 in which said administration is on the first day of menstrual bleeding.

3. The method of claim 1 in which the anordrin is administered in an amount of from about 4 to 8 mg per kg of body weight.

4. The method of claim 1 in which during said period of suppression and prior to resumption of follicular recruitment there is administered by intramuscular injection a second dose of from 2 to 10 mg per kg of body weight, said second dose being effective to continue said total suppression for at least another period of 56 days.

5. The method of totally suppressing ovarian follicular development and related hormonal secretions, comprising administering to a woman having menstrual cycles during a period of menstruation a first dose of from about 4 to 8 milligrams (mg) per kilogram (kg) of body weight of $2\alpha,17\alpha$-diethynyl-A-nor-$5\alpha$-androstane-$2\beta,17\beta$-diol dipropionate, said administration being by intramuscular injection and being given on the first day of menstrual bleeding, the injected amount of anordrin being effective to produce said total suppression for at least 84 days without administration of additional anordrin by any route.

6. The method of claim 5 in which during said period of suppression and prior to the resumption of follicular recruitment there is administered by intramuscular injection a second dose of from about 4 to 8 mg per kg of body weight, said second dose being effective to continue said total suppression for at least another period of 84 days.

* * * * *